(12) United States Patent
Kereth (10) Patent No.: US 8,234,740 B2
(45) Date of Patent: Aug. 7, 2012

(54) MOISTURE BARRIER BREATHING DEVICE

(76) Inventor: Yefim Kereth, Rehovot (IL)

( * ) Notice: Subject to any disclaimer, the term of this patent is extended or adjusted under 35 U.S.C. 154(b) by 487 days.

(21) Appl. No.: 12/523,158

(22) PCT Filed: Jan. 17, 2008

(86) PCT No.: PCT/IL2008/000080
§ 371 (c)(1),
(2), (4) Date: Jul. 14, 2009

(87) PCT Pub. No.: WO2008/087648
PCT Pub. Date: Jul. 24, 2008

(65) Prior Publication Data
US 2010/0071150 A1    Mar. 25, 2010

(30) Foreign Application Priority Data

Jan. 21, 2007   (IL) .......................................... 180820
Apr. 12, 2007  (IL) .......................................... 182484

(51) Int. Cl.
*A47L 1/06*  (2006.01)
(52) U.S. Cl. .......................................... 15/97.1; 15/320
(58) Field of Classification Search ................... 15/97.1, 15/320, 321, 256.5; 134/102.1, 102.2, 104.1
See application file for complete search history.

(56) References Cited

U.S. PATENT DOCUMENTS

| 4,080,685 A | 3/1978 | Vanderpool |
| 4,411,675 A * | 10/1983 | de Castella ..................... 96/140 |
| 5,068,770 A | 11/1991 | Baziuk |
| 5,399,319 A * | 3/1995 | Schoenberger et al. ......... 96/224 |
| 5,402,264 A | 3/1995 | Wilbur |
| 7,584,521 B2 * | 9/2009 | Lobb et al. .................... 15/316.1 |
| 2004/0165352 A1 | 8/2004 | Oyamada |

FOREIGN PATENT DOCUMENTS

| DE | 3107694 | 2/1981 |
| DE | 9303501 | 3/1993 |
| JP | 08190143 | 7/1996 |
| JP | 09212758 | 8/1997 |
| WO | WO 2007-017869 | 2/2007 |

* cited by examiner

*Primary Examiner* — Dung Van Nguyen
(74) *Attorney, Agent, or Firm* — Stetina Brunda Garred & Brucker (57) ABSTRACT

A cleaning assembly (2) for an optical device (16) includes a shaft (14) configured for supporting the optical device within an enclosure (4) that is adapted for rotation about the shaft. At least one first sealing element (18) is disposed between the shaft and a mating surface of the enclosure for preventing fluid leakage therethrough. At least one optically transparent window (8) is mounted in association with the enclosure (4), and at least one cleaning element (9, 11) is coupled to the shaft for cleaning a surface of the window (8). The cleaning assembly may include a moisture barrier in the form of a pressure-influenced member (58) such as a bellows (40) having a body of expandable and retractable-volume for containing air that diffuses therein, while equalizing pressure on opposite sides of the barrier.

8 Claims, 6 Drawing Sheets

MOISTURE BARRIER BREATHING DEVICE

FIELD OF THE INVENTION

The present invention relates to the cleaning of windows in optical instrument housings for removal of dirt and/or other contaminators.

BACKGROUND OF THE INVENTION

Rotatable windows that are automatically cleaned by a stationary cleaning element (e.g., wiper) without obscuring an observer's field-of-view are known per se. Reference is made, for example, to JP56169475, Dec. 26, 1981, which discloses a device for cleaning a TV camera comprising a rotating plate, a lower part of which is immersed in a water tank and which is rotated by an output shaft of a geared motor. A water-proof seal is to provided between the plate and a camera housing to avoid the water immersion in the camera housing. Current problems that militate against the implementation of rotatable windows and stationary cleaning elements for use with electro-optical assemblies include the high friction of the window's dynamic sealing element, commonly used to protect the instrument housing from environment influences, and the high power and complexity of the driving line. In conventional configurations, where the dynamic sealing element is located between the window and the housing, the larger the diameter of the window, the higher is the friction and therefore the higher the power and the complexity of the driving line. Owing to the necessity of keeping the optical window and the housing of the cleaning device sealed, the possibility of reducing the friction in conventional configurations is limited.

Another problem associated with the cleanliness of moisture-sensitive equipment in general, and optically transparent devices in particular, relates to the need to protect the equipment from the effects of moisture. One way to accomplish this is to seal the equipment housing. However, the sealed housing may be exposed to significant pressure differentials driven by temperature and/or altitude variations thus requiring the housing/container to be built from suitably strong material and adding to its cost. To avoid heavy and costly packaging, breather valves are commonly used. These valves prevent excessive pressure differentials caused by temperature and/or altitude variations, but allow ambient air to enter into the interior of the housing/container.

SUMMARY OF THE INVENTION

It is therefore a broad object of the present invention to provide a cleaning assembly for an optical device, the assembly having an optically transparent window that is rotated relative to a cleaning element. It is a particular object of the invention to enable, in a cost-effective way, the rotation of the optically transparent window with significantly lower friction, power consumption and driving-line complexity, while improving the sealing level of the housing.

It is a further object of the present invention to reduce the pressure gradient between the interior of the housing and the ambient air and to minimize the penetration of water to vapors into the interior of the housing.

In accordance with a first aspect of the present invention there is therefore provided a cleaning assembly for an optical device, said cleaning assembly comprising:

a shaft configured for supporting the optical device within an enclosure that is adapted for rotation about said shaft, at least one first sealing element disposed between said shaft and a mating surface of the enclosure for preventing fluid leakage therethrough, at least one optically transparent window mounted in association with the enclosure, and at least one cleaning element coupled to the shaft for cleaning a surface of the window.

In accordance with a second aspect of the present invention there is provided a moisture-barrier breathing device, comprising:

a rigid housing configured to contain at least one moisture-sensitive device;

an opening formed in a wall of said housing for accommodating therethrough a water vapor barrier tube of predetermined geometry and being adapted to be sealed to an exterior of said tube, and at least one pressure-influenced member having a body of expandable and retractable-volume hermetically connected to an end of said tube for containing gas that diffuses therein, while equalizing pressure on both ends of said tube thus ensuring that the tube behaves as an efficient barrier

BRIEF DESCRIPTION OF THE DRAWINGS

In order to understand the invention and to see how it may be carried out in practice, embodiments will now be described, by way of non-limiting example only, with reference to the accompanying drawings, in which.

With specific reference now to the figures in detail, it is noted that the particulars shown are by way of example and for purposes of illustrative discussion of embodiments of the present invention only, and are presented in the cause of providing what is believed to be an enabling description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF EMBODIMENTS

In the following description of some embodiments, identical components that appear in more than one figure or that share similar functionality will be referenced by identical reference symbols.

Figure 1A:
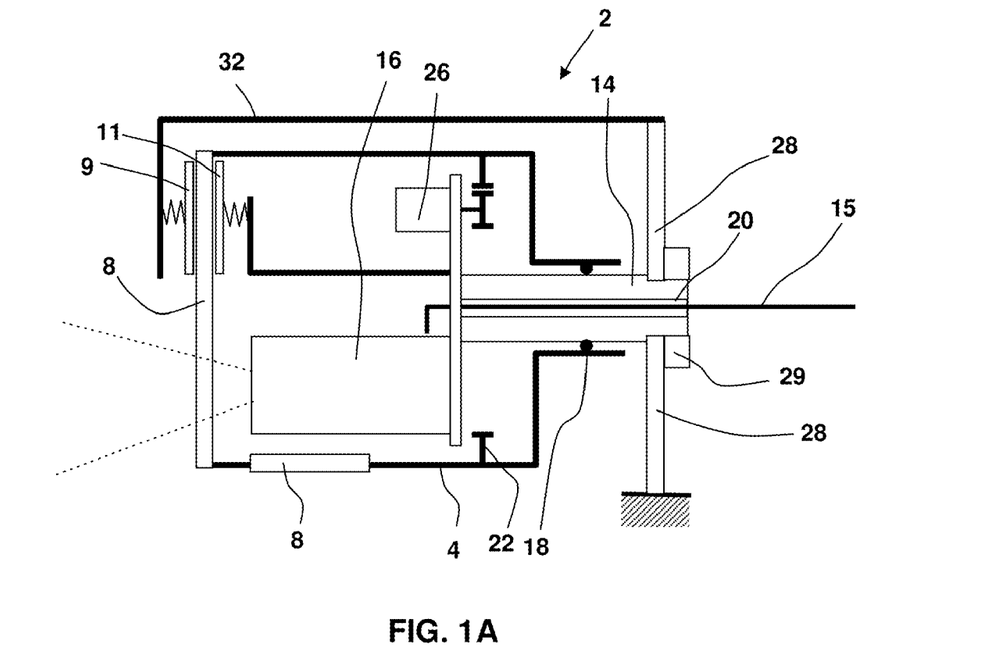
FIGS. 1A and 1B are simplified schematic side cross-sectional views of a cleaning assembly according to first and second embodiments of the invention, respectively.
Figure 1B:
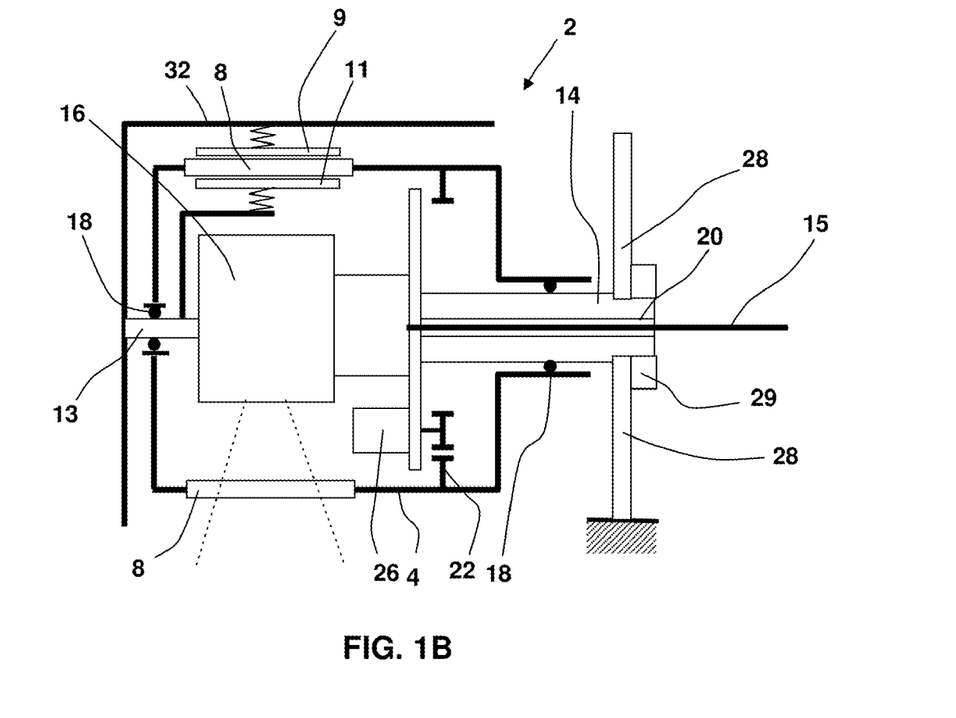

FIGS. 1A and 1B are simplified schematic side cross-sectional views of a cleaning assembly according to first and second embodiments of the invention, respectively, detailed views of which are shown in FIGS. 2A to 2E. As best seen in FIG. 1A, the cleaning assembly 2 comprises an enclosure 4 for accommodating therein an electro-optical device 16 (constituting an optical device). In FIG. 1A the optical device 16 is shown as having an optical axis parallel to a longitudinal axis of the enclosure 4. However, it may also be transverse thereto as shown in FIG. 1B. The enclosure 4 is adapted for rotation about a shaft 14 which supports the optical device. The shaft 14 is anchored to a stationary structure 28 via a flange nut 29 and includes a bore 20 for accommodating external electrical connection to lines 15 for coupling to the optical device. In order to prevent leakage of fluid such as moisture or air into the enclosure, a dynamic seal 18 (constituting a first sealing element) is disposed between the shaft 14 and a mating surface of the enclosure. At least one optically transparent window 8 is mounted in association with the enclosure 4. Thus, in the figure there are shown two such windows (FIG. 1A), one being mounted at an end of the enclosure and the other being mounted in a side surface thereof for transmitting radiation to and from optical devices whose axes are respectively parallel or transverse to the longitudinal axis of the enclosure. At least one cleaning element is coupled at least indirectly to the shaft 14 for cleaning a surface of the window 8 and may include an external cleaning element 9 for cleaning an outer surface of the window and/or internal cleaning element 11 for cleaning an inner surface of the window.

In FIG. 1A, where the cleaning elements 9 and 11 are adapted to clean by contact pressure with the window 8, the optical device 16 is mounted eccentrically relative to the shaft 14 and the cleaning elements 9 and 11 are resiliently biased so as to maintain contact with a periphery of respective outer and inner surfaces of the window 8 without obscuring the field of view of the optical device. The cleaning elements are dimensioned so that complete rotation of the enclosure 4 around the shaft 14 induces the cleaning elements to clean at least an annular periphery of the window's surface of sufficient size to overlap the field of view of the optical device 16, thus improving visibility of the optical device 16. In FIG. 1B, the window 8 is formed in the side wall of the enclosure and the cleaning elements 9 and 11 are again resiliently biased so as to maintain contact with opposing outer and inner surfaces thereof without obscuring the field of view of the optical device. In both cases, suitable contact or non-contact cleaning elements may be used such as brushes, wipers, sprinklers, heaters, vents, air-jets, water-jets and so on. In the case of non-contact cleaning elements such as air-jets and water-jets, it is of course not necessary that they be resiliently biased since they do not need to maintain contact with the window's surfaces.

The cleaning elements are supported by a structure that is independent of the enclosure such as a shield 32 supported directly or indirectly by the shaft 14. Thus, in FIG. 1A, the shield 32 is simply an overhanging bracket that is anchored at one end indirectly to the shaft 14 and at its opposite end supports the cleaning elements in proper disposition relative to the optically transparent window. In FIG. 1B, the shield 32 is anchored to the optical device 16 via an auxiliary shaft 13 that protrudes through the end face of the enclosure. In order to prevent fluid leakage through the enclosure where it meets the auxiliary shaft 13, an additional dynamic seal 18 is required. In this embodiment, cleaning of the optically transparent window 8 can be achieved just by the pan or tilt motion of the optical device 16, while the enclosure 4 is slowed or stopped by activation of a solenoid (not shown), which is at least indirectly carried by the structure 28. An additional way to clean the optically transparent window 8 is to rotate the optical device 16 beyond its nominal angular range. In this case the cleaning elements, indirectly attached to the shaft 14 and the structure 28, are located outside the normal angular range of the field of view of the device 16 so as not to obscure its visibility under normal use, and will briefly obscure its field of view only during rotation of the enclosure beyond the normal range.

Also shown schematically in FIGS. 1A and 1B is a motor 26 that is fixedly attached to the shaft 14 and that drives the enclosure via a drive mechanism 22, which may be a gear train or belt drive. Operating the motor 26 causes the enclosure 4 to rotate about the shaft 14, thus inducing relative movement between the cleaning elements, which are anchored to the shaft, and the optically transparent window 8 and cleaning whichever surface of the window 8 is served by the respective cleaning element.

In the arrangement shown in FIGS. 1A and 1B, the force required to make the enclosure 4 rotate about the shaft 14, that is of significantly lower diameter than that of the window 8 itself, is significantly reduced compared to what would be required if the rotation were applied between the window 8 and the circumference of the enclosure 4.

Figure 2A:
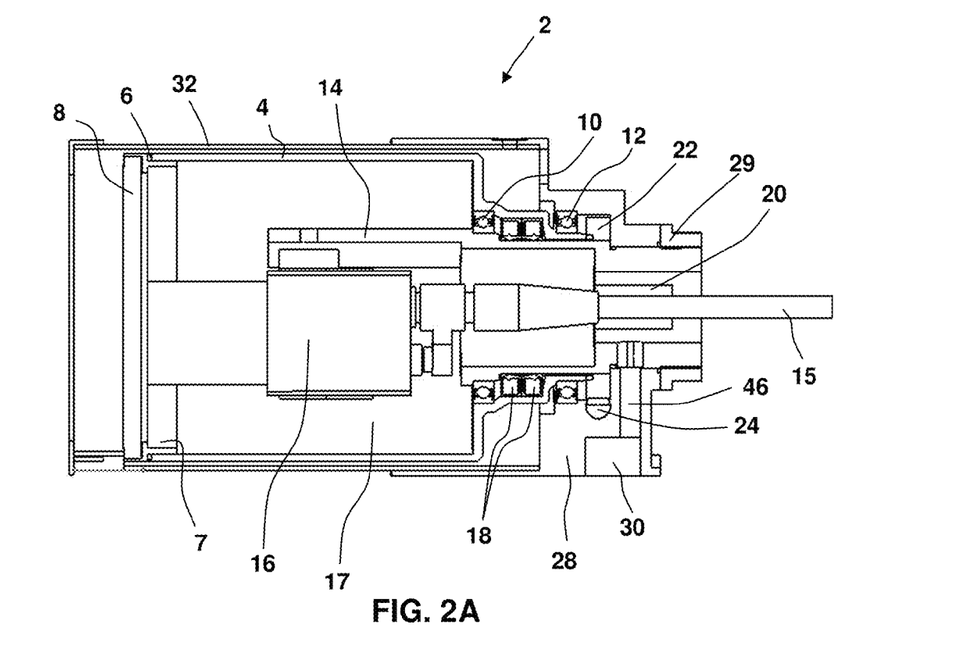
FIG. 2A is a detailed side cross-sectional view of the cleaning assembly shown in FIG. 1A.
Figure 2B:
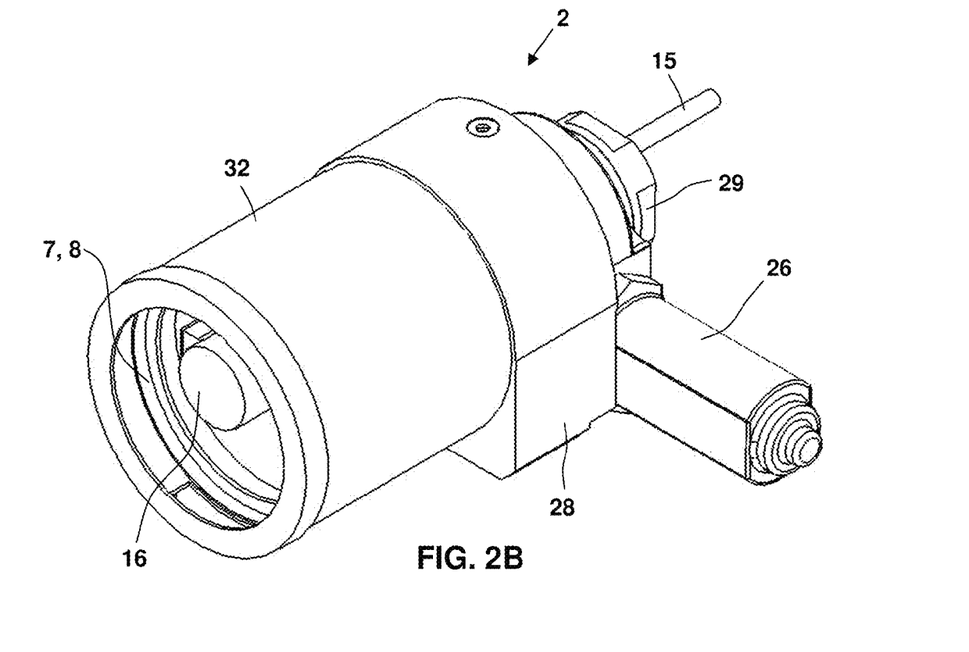
FIGS. 2B and 2C are perspective views of the assembly shown in FIG. 2A.

Referring now to FIG. 2A, it is shown in more detail that the assembly 2 comprises a cylindrical enclosure 4 that is coupled to an optically transparent window 8 that is threadably connected to the enclosure and sealed by an "O" ring 6 (constituting a second sealing element), after prior insertion and fixing of the optical device 16. The enclosure 4 is rotatable by two ball bearings 10 and 12 about a shaft 14 which at least indirectly supports an electro-optical instrument 16 (e.g., camera). A circumferential sector (e.g. ring) of the enclosure 4 can be formed of radiation-transmittable material (as shown in FIG. 2B) thus providing an optically transparent window through which optical signals can pass. This is useful for optical devices having pan and/or tilt movement as well as for optical devices that have a field-of-view transverse to the axis of the enclosure. The dimension/diameter of the optically transparent window 8 can be as large as necessary for installing one or more electro-optical devices and its associated electronics inside the enclosure and for affording sufficient field-of-view for the electro-optical device. The cylinder 4 coupling with the shaft 14 is sealed by a pair of dynamic sealing elements 18 (constituting first sealing elements) for preventing fluid leakage into the interior of the enclosure. The shaft 14 at its rear end is provided with a bore 20 of sufficient diameter to accommodate therethrough power and/or communication and/or command lines 15 for coupling to the optical device. After insertion of the lines, the bore 20 is sealed to prevent penetration of ambient air and environmental contaminants into the enclosure. Therefore, the shaft 14 diameter at the location of the dynamic sealing elements 18 can be significantly smaller than the diameter of the optically transparent window 8. Consequently, the friction during the rotation can be significantly lower and the sealing level can be significantly higher. The enclosure 4 is coupled at its rear end to a spur wheel 22 driven by a worm gear 24 and powered by an electric motor 26. The electric motor can be located inside the enclosure as well, as shown in FIGS. 1A and 1B, and other driving line/transmission configurations (e.g., friction wheels, belts, spur wheels) between the motor and the enclosure are also feasible.

The shaft 14 is coupled to a structure 28 by a nut 29, and optionally communicates via the bore 20 and via a bore 46 in the structure 28 with a breathing/relief valve 30 (constituting a pressure release valve). The purpose of the valve 30 is to prevent collapse or deformation of the enclosure under extreme pressure gradients, by allowing two-directional "breathing" when the pressure gradient reaches a certain predefined level, which need not be symmetrical for intake and outtake. External contact and non-contact cleaning elements, e.g., wiper 9 (FIG. 2D), brush and sprinkler (not shown), are carried by the shield 32, which is coupled to the structure 28. Whenever mud/rain/dust or other contaminators contaminate the exterior of the radiation-transmittable surface 8, it can be simply removed by a rotation of the enclosure 4 constituted by the cylindrical body and optically transparent window 8 relative to the exterior cleaning elements, driven by the electric motor 26. The internal cleaning element, e.g., wiper 11 (FIG. 2E), is at least indirectly carried by a shaft 14 and optionally resiliently biased toward the interior surface of the optically transparent window 8, so as not to obscure the field-of-view of the electro-optical device 16 during normal use of the device. Whenever water vapor condenses on the interior of the optically transparent window 8, it can be simply removed by a rotation of the enclosure 4 relative to the interior cleaning element 11, driven by the electric motor 26. To avoid water vapor condensation on the lens surfaces of the electro-optical device 16, the lens surfaces can be heated above the to dew point by a heater (not shown). This arrangement, of internal cleaning, allows a higher level of relative humidity inside the enclosure to be tolerated, and therefore allows filling the interior of housing just with a dry air, instead of nitrogen.

Water vapor, initially captured within the enclosure 4 during installation, or that enters through the relief valve 30, is absorbed by a small amount of drying agent/desiccant (not shown) disposed inside the enclosure. To reduce the amount of desiccant, the volume of air/gas captured within the housing can be decreased to a minimum by any suitable filler material 17 (shown in FIGS. 2A, 2D and 2E) such as plastic, balls of foam or polystyrene. The lower volume of captured air/gas thus resulting will give rise to a lower demand for intake/discharge through the breather.

The device 2 may be made in a variety of shapes and sizes as required for accommodating optical devices 16, such as cameras, optical elements, sensors, and the like. The enclosure may be made of a single unit or assembled from more than a single unit.

The device 2, while powered by an electric or other motor, can be remotely controlled and therefore can fit variety of robotic/unattended applications and/or human-attended missions conducted under harsh environmental conditions.

Figure 2C:
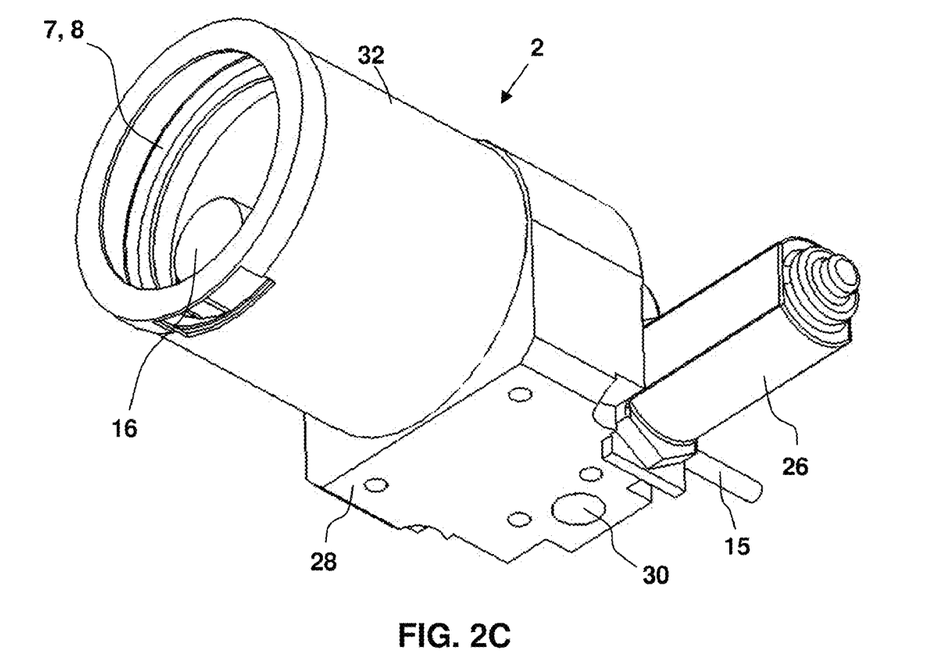

FIGS. 2B and 2C are perspective views of the assembly shown in FIG. 2A showing better the eccentric mounting of the optical device 16 within the cylindrical enclosure 4. Also shown in better detail is the attachment of the motor 26 and the relief valve 30.

Figure 2D:
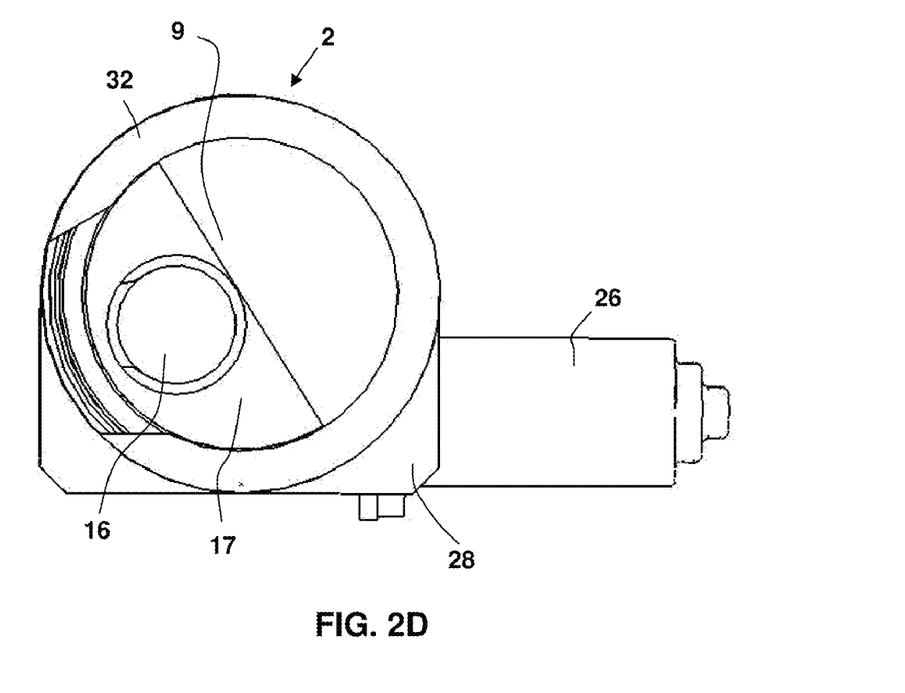
FIGS. 2D and 2E are front elevations of the assembly shown in FIG. 2A showing details of cleaning elements according to different embodiments of the invention.
Figure 2E:
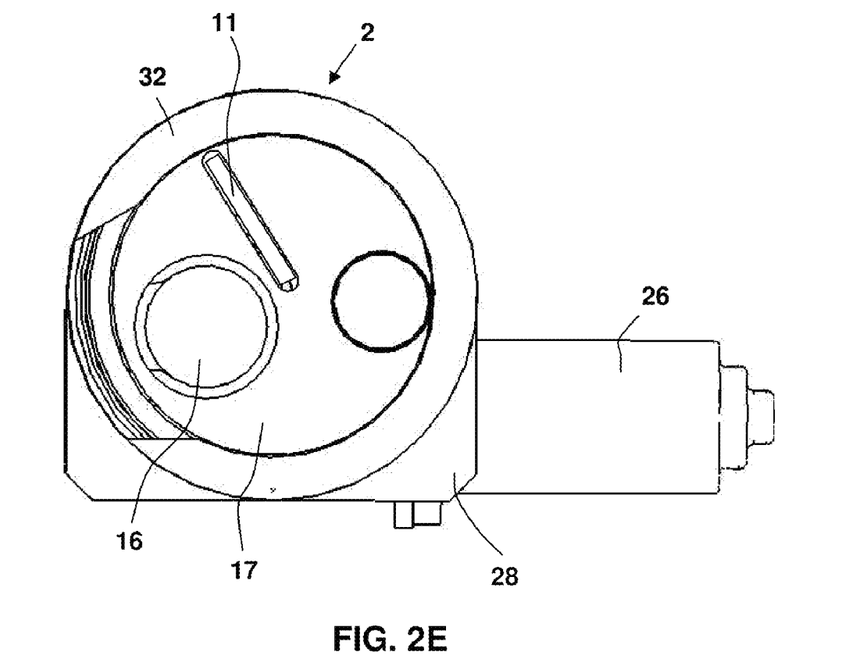

FIGS. 2D and 2E are front elevations of the assembly shown in FIG. 2A showing respectively the external cleaning element 9, the internal cleaning element 11 and the filler material 17 according to different embodiments of the invention. In FIG. 2D the optical device 16 field of view is disposed completely within one half of the enclosure 4 so as to intersect an annular periphery of the window's surface of sufficient size cleaned by the external cleaning element 9. The external cleaning element 9 is a semi-circular leaf wiper that completely covers the window 8 in the opposite half of the enclosure. In FIG. 2E, the internal cleaning element 11 is mounted radially so as not to obscure the optical device field of view.

Figure 3A:
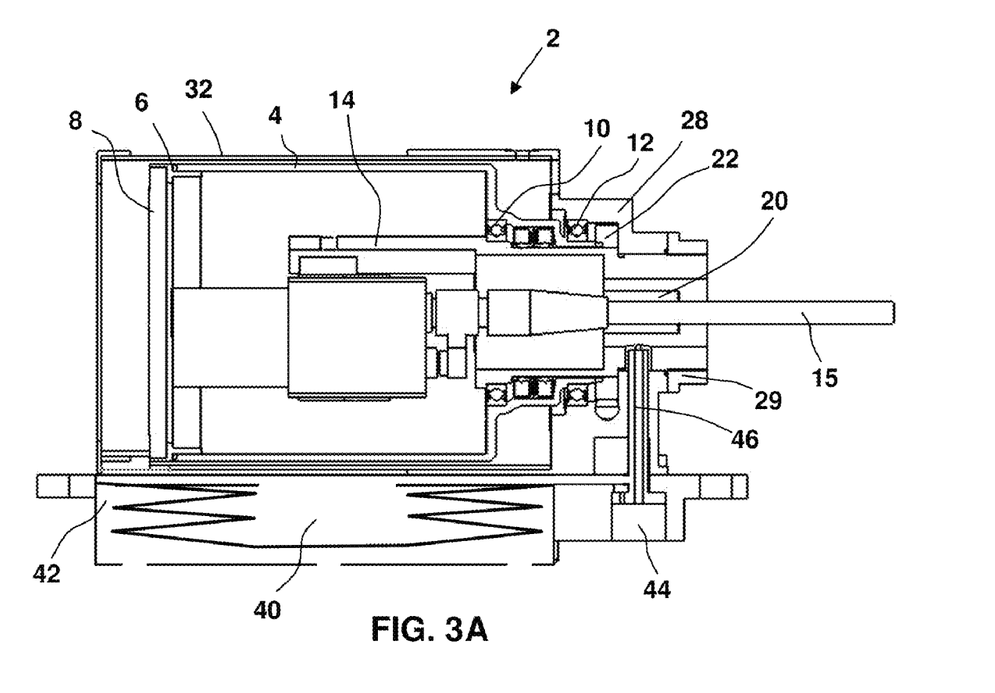
FIG. 3A is a detailed side cross-sectional view of a cleaning assembly according to a third embodiment of the invention.
Figure 3B:
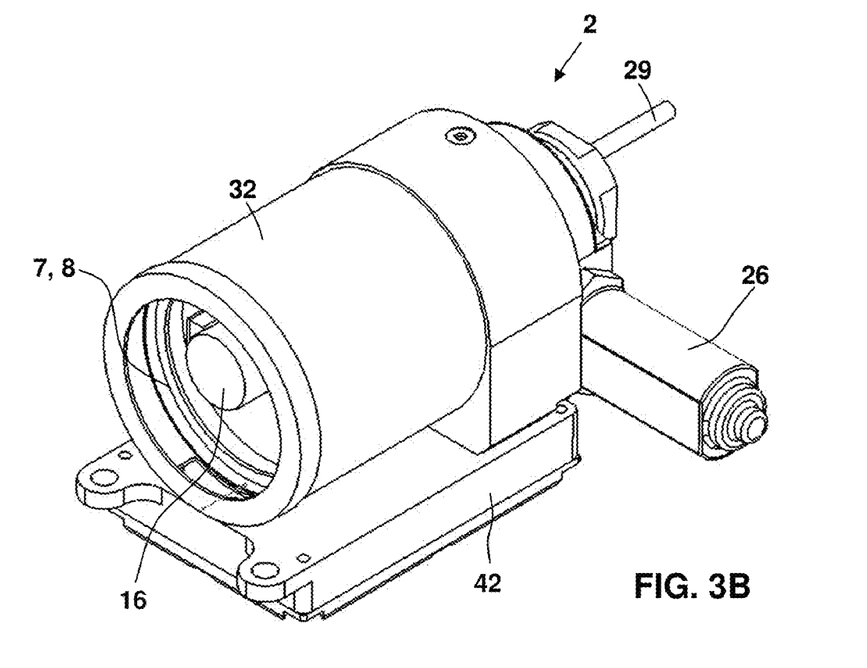
FIGS. 3B and 3C are perspective views of the assembly shown in FIG. 3A.
Figure 3C:
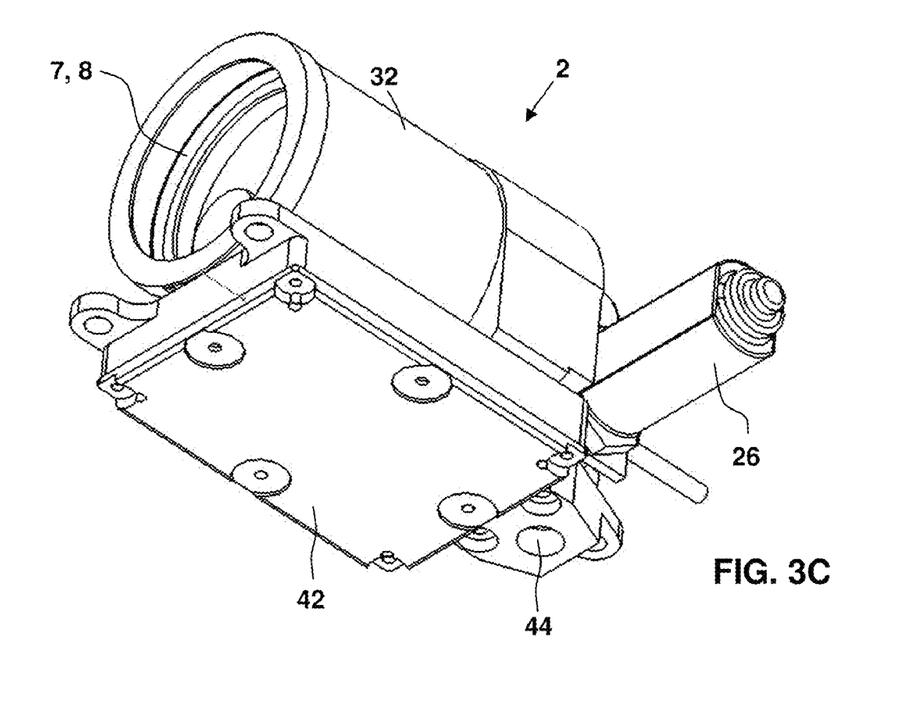

FIG. 3A is a detailed side cross-sectional view and FIGS. 3B and 3C are perspective views of a cleaning assembly 2 having an air/gas capacitor 40. Whenever the exchange of air/gas between the empty space of the enclosure 4 and the ambient air is not acceptable, e.g., under extremely high ambient air humidity, the air/gas capacitor 40, based on a pressure equalization device such as an expandable and retractable bellows, may be applied as a complementary aid for the above. The bellows 40, which may be folded inside an auxiliary chamber 42, is hermetically coupled at its interior to the interior of the enclosure, optionally via the relief valve 30 shown in a FIG. 2A, contains the dry air/gas relieved from the enclosure via the relief valve 30, or alternatively, under the ambient pressure, pushes the previously relieved dry air/gas back into the enclosure through the relief valve 30. The bellows 40 keeps the contained air/gas pressure at the ambient air pressure and therefore avoids entry of contaminated ambient air into the enclosure. An additional relief valve 44, which communicates between the interior of the bellows 40 and the ambient air, is adjusted to relieve at a differential pressure that is beyond the permitted pressure gradient for the bellows 40 and/or the enclosure. In the above configuration the volume of the expandable and retractable bellows 40 and consequently of the complete assembly 2 is minimized Moreover, droplets of water vapor that diffuse via the bellows 40 material will be prevented by the relief valve 30 from entering the enclosure and settling on the active surfaces of the optical device 16.

Alternatively, to stop water vapor that diffuses via the bellows 40 material from getting into the interior of the enclosure 4, the relief valve 30 can be replaced by a moisture barrier based on the Fick's Law. It may be shown based on Fick's Law, that moisture will not pass freely through a tube having a length that is ten or more times its diameter, providing that there is no pressure differential between the two ends of the tube. Given that the pressure differential is eliminated by the expandable and retractable bellows 40 as is generally the case, and that the bore 46 in the structure 28 is adapted to satisfy this length-diameter definition, the diffusion of the water vapor from the interior of the bellows 40 into the interior of the enclosure 4 can be prevented or dramatically reduced.

Although expandable and retractable volume constituted by the bellows 40 has been described with particular regard to its use as an air/gas capacitor in a cleaning assembly for an optical device, it will be understood that it has more general application.

Figure 4:
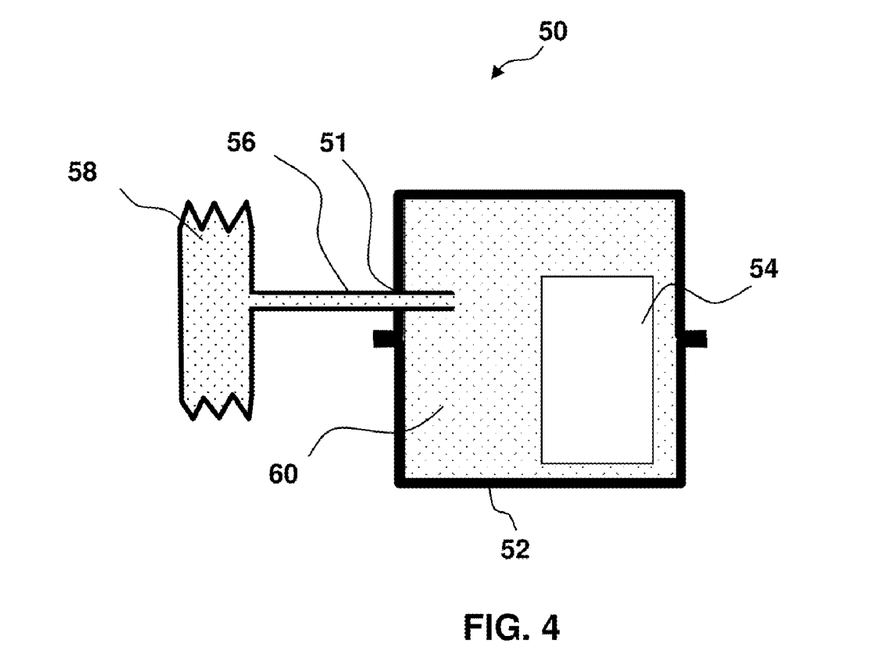
FIG. 4 is schematic cross-sectional view of a moisture-barrier breathing device having an externally located body of expandable and retractable-volume.

FIG. 4 is a cross-sectional view showing schematically a moisture-barrier breathing device 50 employing an expandable and retractable volume according to an embodiment of the invention. The device 50 comprises a rigid housing 52, advantageously a two-part housing, enclosing a moisture-sensitive-item 54 and a gas (not shown), such as air, nitrogen to etc. An opening 51 is formed in a wall of the housing 52 for enabling a barrier tube 56 of predefined cross-sectional size and geometry to pass through the housing 52. The opening 51 is adapted to be sealed to the exterior side of said barrier tube 56. At least one pressure-influenced member 58 in the form of a body having an expandable and retractable-volume communicates with one of the ends of the tube for containing the diffused gas while equalizing the pressure on both ends of the tube 56 thus ensuring that the tube behaves as an efficient barrier. The housing 52 delimits an interior space 60 communicating with the expandable and retractable body 58 via the tube 56.

To prevent condensation of residual moisture, which could be trapped during installation and/or as a result of diffusion into the housing space over time, a small amount of desiccant (not shown) is stored inside the housing 52, or inside the member 58.

Whenever there is a positive pressure gradient between the ambient and the interior of the housing 52, the differential pressure constitutes a pressure gradient that causes the volume of the pressure-influenced member 58 to be reduced. Under the influence of the pressure gradient some of the gas contained inside the member 58 will flow via the tube 56 into the interior of the housing 52. This flow will stop when the pressure on both ends of the tube 56 is equalized. The water vapor content contained inside the member 58 normally should be lower than the average ambient water vapor content, if materials of appropriate diffusion resistance and geometry are chosen for the member 58. Consequently, the amount of water vapor that diffuses into the housing 52 via the tube 56 under the positive pressure gradient will be smaller than it could be if the tube 56 end was exposed directly to the ambient air.

A negative pressure gradient between the ambient and the interior of the housing 52 will cause the volume of the pressure-influenced member 58 to increase. Under the influence of such a negative pressure gradient some of the gas contained inside the housing 52 will flow via the tube 56 into the interior of the member 58. This flow will stop when the pressure on both ends of the tube 56 is equalized. The dry gas diffused into the member 58 via the tube 56 will mix with the previously contained gas of member 58 and the resulting mixture will feed into the housing 52 once the pressure gradient becomes positive.

Figure 5:
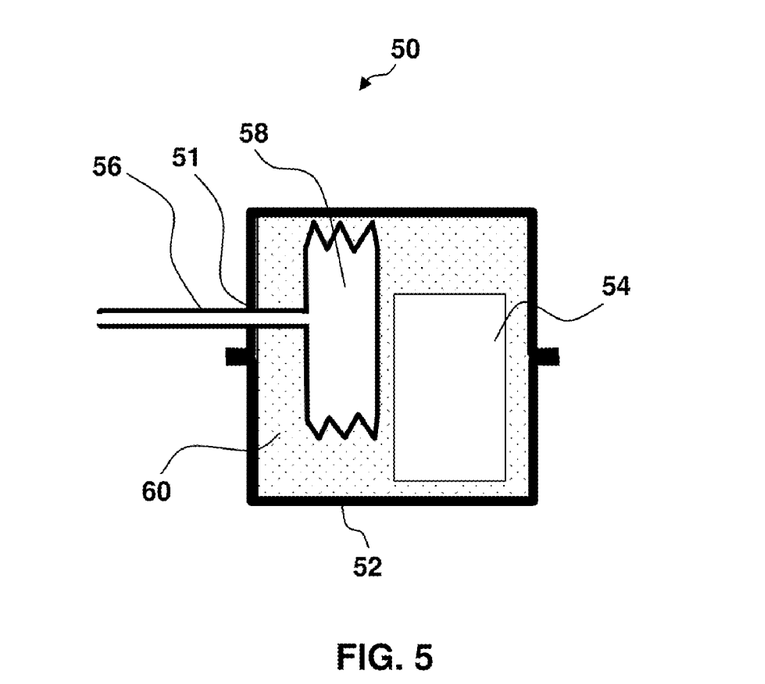
FIG. 5 is schematic cross-sectional view of a moisture-barrier breathing device having internally located body of expandable and retractable-volume.

It should be understood that the member 58 may equally be located inside the housing 52 as it shown in FIG. 5. In this case the interior space 60 is delimited by the housing 52 and to the exterior of the expandable and retractable-volume, body 58, which communicates with the atmosphere via the barrier tube 56. The operation of this embodiment is similar to that described above.

The device 50 may be made in a variety of shapes and sizes as required for placing the material or equipment inside. The housing 52 may be made of a single enclosure or assembled from more than a single component and it may be constructed from a variety of materials, optionally transparent or having at least one transparent wall, to support the functionality of the enclosed equipment.

It will be evident to those skilled in the art that the invention is not limited to the details of the foregoing illustrated embodiments and that the present invention may be embodied in other specific forms without departing from the essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

In particular, while one embodiment of the invention has been described with particular reference to an electro-optical device requiring coupling to external power and control lines, it will be appreciated that similar principles apply also to other optical devices.

What is claimed is:

1. A moisture-barrier breathing device, comprising:
    a rigid housing configured to contain at least one moisture-sensitive device;
    an opening formed in a wall of said housing for accommodating therethrough a water vapor barrier tube of predetermined geometry and being adapted to be sealed to an exterior of said tube, and
    at least one pressure-influenced member having a body of expandable and retractable-volume hermetically connected to an end of said tube for containing gas that diffuses therein, while equalizing pressure on both ends of said tube thus ensuring that the tube behaves as an efficient barrier;
    said predetermined geometry being such that a length of the vapor barrier tube is at least ten times its diameter so as to prevent diffusion of water vapor from the pressure-influenced member into the rigid housing.

2. The device according to claim 1, wherein said housing is a two-part housing.

3. The device according to claim 1, wherein at least one wall of the housing is transparent.

4. The device according to claim 1, wherein the at least one pressure-influenced member is formed of a fluid impermeable material.

5. The device according to claim 1, wherein the at least one pressure-influenced member is disposed outside said housing and communicates with an interior of the housing via the barrier tube.

6. The device according to claim 1, wherein the at least one pressure-influenced member is disposed inside said housing and communicates with atmosphere via said barrier tube.

7. The device according to claim 1, wherein the housing contains a desiccant.

8. The device according to claim 1, wherein said at least one pressure-influenced member contains a desiccant.

* * * * *